(12) United States Patent
Godin

(10) Patent No.: US 6,764,518 B2
(45) Date of Patent: Jul. 20, 2004

(54) PROSTHESIS FOR CONTROLLING THE DIRECTION OF FLOW IN A DUCT OF A LIVING ORGANISM

(75) Inventor: Norman Godin, Geneve (CH)

(73) Assignee: Biomedix S.A., Fribourg (SE)

( * ) Notice: Subject to any disclaimer, the term of this patent is extended or adjusted under 35 U.S.C. 154(b) by 0 days.

(21) Appl. No.: 10/170,115

(22) Filed: Jun. 12, 2002

(65) Prior Publication Data

US 2003/0009236 A1 Jan. 9, 2003

Related U.S. Application Data

(63) Continuation of application No. PCT/CH00/00465, filed on Sep. 1, 2000.

(30) Foreign Application Priority Data

Dec. 13, 1999 (EP) .............................. 99811143

(51) Int. Cl.[7] .............................. A61F 2/36; A61F 2/04; A61F 2/06
(52) U.S. Cl. .................................................. 623/23.68
(58) Field of Search ........................... 623/23.64–23.7, 623/1.13, 1.15

(56) References Cited

U.S. PATENT DOCUMENTS

| 5,314,473 | A | * | 5/1994 | Godin .................... 623/23.68 |
| 5,476,506 | A | * | 12/1995 | Lunn ...................... 623/1.28 |
| 5,769,887 | A | * | 6/1998 | Brown et al. .............. 623/1.23 |
| 5,820,584 | A | | 10/1998 | Crabb |
| 5,855,601 | A | * | 1/1999 | Bessler et al. ............. 623/2.38 |
| 6,152,956 | A | * | 11/2000 | Pierce ...................... 623/1.13 |
| 6,302,917 | B1 | * | 10/2001 | Dua et al. ................ 623/23.68 |
| 6,383,171 | B1 | * | 5/2002 | Gifford et al. .............. 604/508 |
| 6,395,019 | B2 | * | 5/2002 | Chobotov .................. 623/1.13 |
| 6,544,291 | B2 | * | 4/2003 | Taylor ..................... 623/63.68 |
| 6,675,809 | B2 | * | 1/2004 | Stack et al. ................. 128/898 |
| 2001/0049553 | A1 | * | 12/2001 | De Paulis .................. 623/1.24 |
| 2003/0060894 | A1 | * | 3/2003 | Dua et al. ................ 623/23.68 |

FOREIGN PATENT DOCUMENTS

| FR | 2 694 688 | 11/1992 |
| WO | WO 91 01117 | 7/1991 |
| WO | WO96/29954 | 10/1996 |

* cited by examiner

Primary Examiner—David H. Willse
Assistant Examiner—Suzette J. Jackson
(74) Attorney, Agent, or Firm—Sturm & Fix LLP

(57) ABSTRACT

The invention relates to a generally tubular prosthesis (1) for controlling the direction of flow in a duct (O) of a living organism. Said prosthesis consists of a biocompatible, elastically deformable material and comprises an annular proximal fixing part (1a) in a section (H) of the duct (O) with a greater diameter; and a distal part (1b) whose wall is designed in such a way that it can collapse on itself in the event that an overpressure is exerted on its outer surface. The diameter of said annular proximal fixing part (1a) is substantially equal to that of said section (H) of the duct (O) with a greater diameter and its resistance to crushing is significantly greater than that of the distal part (1b) of the prosthesis (1), so that the annular proximal part (1a) can retain the prosthesis (1) in the duct (O) of the living organism.

24 Claims, 2 Drawing Sheets

PROSTHESIS FOR CONTROLLING THE DIRECTION OF FLOW IN A DUCT OF A LIVING ORGANISM

CROSS REFERENCE TO RELATED APPLICATIONS

This application is a Continuation application of PCT/CH00/00465 filed Sep. 1, 2000, which claimed priority of European Patent Application No. 99811143.9 filed Dec. 13, 1999, entitled "Prosthesis for Controlling the Direction of Flow in a Duct of a Living Organism" all of which are including in their entirety by reference made hereto.

BACKGROUND OF THE INVENTION

1. Field of the Invention

The present invention relates to a prosthesis of generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, and also relates to a method for fitting this prosthesis.

2. Description of the Prior Art

Such prostheses have in particular been proposed for controlling gastric reflux into the esophagus in persons suffering generally from a hiatal hernia accompanied by reflux esophagitis. This repeated reflux of gastric acid attacks the wall of the esophagus and eventually leads to esophagitis which is manifested by ulceration of the wall and sometimes by a narrowing of its cross section. It has been proposed, particularly in WO 96/29954, to provide a prosthesis intended to permit the flow of food from the esophagus to the stomach but to stop the reflux of the gastric content from the stomach into the esophagus under the reflux pressure by means of folding in and/or "collapsing". The problem with such prostheses lies in how they are fixed and in how they are changed, in other words their fitting and removal. In fact, as this condition is a chronic one, a patient will have to be equipped with such a prosthesis on a continuous basis, so that the latter will need to be changed periodically, especially as a result of the aging of the materials used, generally elastomers, and the particularly aggressive conditions of the environment in which it is located, the gastric acid having a pH of the order of 1. The only solutions proposed however are either surgical or involve fastening elements of an unspecified nature. The surgical route would only really be acceptable if the prosthesis could be guaranteed for the lifetime of the patient. However, it is well known that all elastomers age and that the environment in which the prosthesis is intended to function is also particularly aggressive, so that the surgical route does not represent a solution because it would have to be performed periodically, whereas there are other drug-based therapeutic routes including antacids which tend to render the environment neutral, H2 antihistamines which fix to the H2 receptors of the parietal cell, and medicines which block the production of H+ ions by the parietal cell. A common feature of these medicines is that they do not cure the illness from which the patient is suffering, with the result that they have to be administered continuously. It is clear at present that none of the solutions proposed is satisfactory, given that they only offer a choice between continuous administration of medicines and repeated surgical interventions.

It is clear that the prosthesis constitutes without doubt the best potential solution in that it allows the dysfunction from which the patient is suffering to be remedied by purely mechanical means. However, this solution only becomes feasible if the fitting and removal of this prosthesis can be done by the endoscopic route.

BRIEF SUMMARY OF THE INVENTION

It is precisely the object of the present invention to propose a solution which permits fitting and removal of the prosthesis by the endoscopic route.

To this end, the present invention relates to a prosthesis of generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, characterized in that said annular proximal fixing part is associated over a certain width with stiffening means for giving it a resistance to crushing which is greater than that of the distal part of the prosthesis, able to retain the prosthesis by applying said annular proximal part against the wall of said section of greater diameter of said duct with a force sufficient to ensure that it is held in place as the food bolus passes through it.

The present invention also relates to a method for fitting this prosthesis wherein the temperature of the element made of shape-memory alloy is first lowered at least to its lower temperature limit of its temperature range of martensitic transformation, the diameter of said prosthesis is then reduced to allow it to be placed in a hiatal hernia, the element made of shape-memory alloy is freed from its constraint and it is heated until its temperature reaches at least the upper limit of its austenitic transformation temperature and it recovers its initial shape.

It is precisely the object of the present invention to propose a solution which permits fitting and removal of the prosthesis by the endoscopic route.

To this end, the present invention relates to a prosthesis of generally tubular shape as claimed in claim 1 and to a method for fitting this prosthesis as claimed in claim 12.

BRIEF DESCRIPTION OF THE DRAWINGS

The attached drawing illustrates, diagrammatically and by way of example, two embodiments of the prosthesis forming the subject of the present invention.

DETAILED DESCRIPTION OF THE INVENTION

Figure 1:
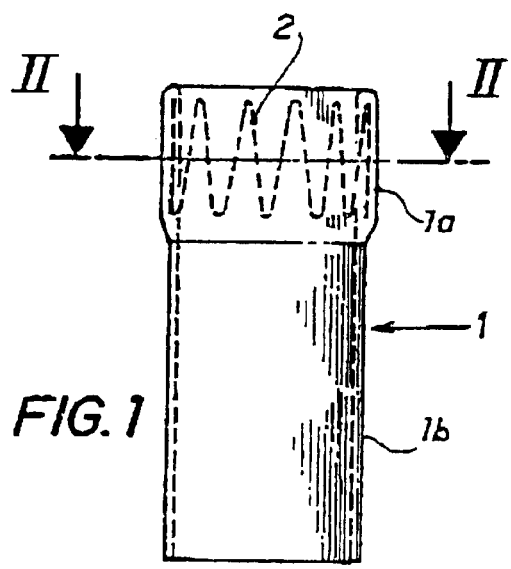
FIG. 1 is an elevation view of a prosthesis according to this embodiment.
Figure 2:
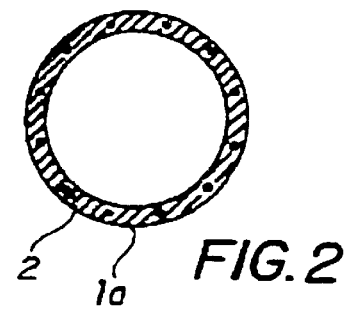
FIG. 2 is a cross section along II—II in FIG. 1.

In FIG. 1, a tubular prosthesis 1 is shown which is molded in one piece with an annular proximal fixing part 1a having a greater resistance to crushing than the distal part 1b. This prosthesis 1 is intended to prevent esophageal reflux. Such a prosthesis is described in detail in WO 96/29954 to which reference can be made for further details.

This tubular prosthesis 1 is made of a biocompatible elastomer, for example a silicone-based elastomer with two components of medical quality sold under the brand name Silastic® by Dow Corning Corp, or a silicone from the Nusil company. Rubbers of the butyl type can also be used. These materials and their thickness are chosen so that, in the presence of an overpressure exerted on the outer face of the distal part of the tubular prosthesis 1, its walls join each other and thus prevent passage of substance from the stomach to the esophagus.

Figure 6:
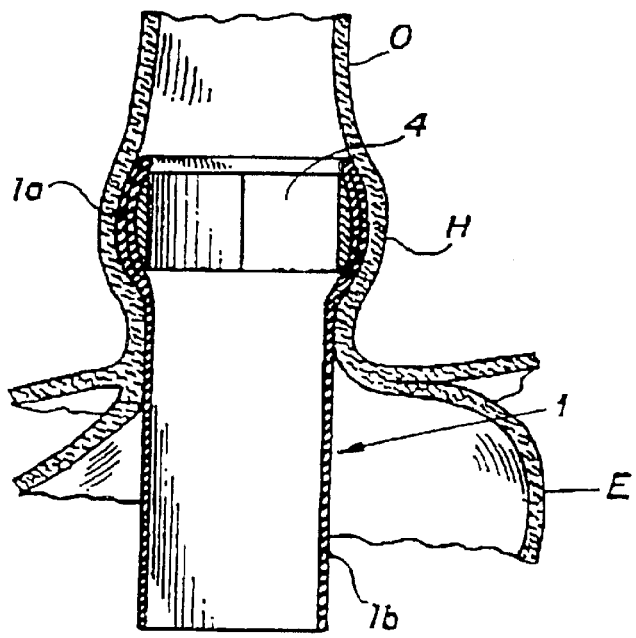
FIG. 6 is a cross section of the base of the esophagus and the top of the stomach, with the proximal end of the prosthesis fixed in a hiatal hernia.

An elastic reinforcing or stiffening element 2 is embedded in the annular proximal part 1a of the prosthesis 1 in order to form an annular fixing part. This elastic element 2 must exert a centrifugal force intended to apply the proximal end 1a of the prosthesis 1 against the wall of the duct of the organism in which it is to be placed, this duct in this example being the hiatal hernia presented by most patients suffering from chronic gastric reflux, as is illustrated in FIG. 6. This elastic reinforcing element 2 must at the same time be sufficiently retractable following application of a centripetal force to make it possible to very substantially reduce its cross section with a view to its insertion into the duct of the living organism by the endoscopic route, and its removal from said duct.

Figure 3:
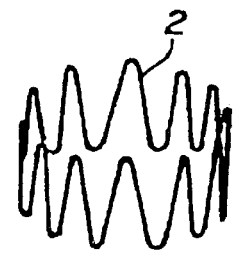
FIG. 3 is a perspective view of a detail of an element for stiffening the proximal end of the prosthesis.

For this purpose, the elastic reinforcing element can have different forms, such as that illustrated in FIG. 3 in which the elastic reinforcing element is formed by a spring wire 10 arranged in a ring of a certain width, forming regular meanders from one edge of the ring to the other. This elastic element 2 can be made, for example, of a nickel/titanium shape-memory alloy permitting considerable deformation during fitting and removal, or of medical-grade spring steel. An elastomer in which the elastic element 2 is embedded is biocompatible and protects the wall of the tissues from any damage due to the elastic element and prevents displacement of the prosthesis.

The elastic reinforcing or stiffening element 2 can be strongly deformed by a centripetal force in order to reduce its cross section and allow it to be introduced by the endoscopic route.

As is illustrated in FIG. 6, the prosthesis 1 is fixed between the base of the esophagus O and the top of the stomach E, generally in a part formed by a hiatal hernia H. The part of the prosthesis 1 which is used for fixing it is the proximal part 1a whose resistance to crushing is substantially greater than that of the rest of the tubular element 1 and in which the elastic reinforcing element 2 is embedded. It will be seen in this FIG. 6 that a slotted ring 4 is arranged inside the annular proximal fixing part 1a.

Figure 4:
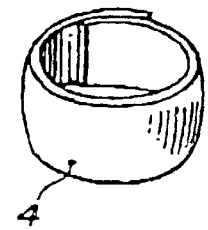
FIG. 4 is a perspective view of another element for stiffening the distal end of the prosthesis in the contracted state.
Figure 5:
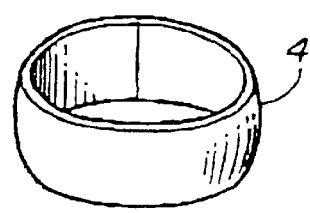
FIG. 5 is a perspective view of the element illustrated in FIG. 4 in the noncontracted state.

This slotted ring 4 is an elastic ring capable of winding up in a coil, as is illustrated in FIG. 4, when a centripetal pressure is applied to it. On releasing it, it recovers its initial cross section, as is illustrated in FIG. 5. To allow it to match the shape of the hernia, its outer face can advantageously have a convex bulge, as is seen in particular in FIGS. 4 and 5. It is obviously also possible to use a spring leaf of equal thickness and to bend it in its width.

By choosing a size appropriate to the diameter of the hiatal hernia H, the slotted elastic ring 4 makes it possible to exert a centrifugal pressure on the annular fixing part 1a of the prosthesis 1, able to maintain this prosthesis in place with sufficient force to ensure that it is held in position while resisting the passage of the food bolus through it. The material used to form the elastic ring can be a metal, such as stainless steel, or a sufficiently rigid and elastic plastic material, or alternatively a metal coated with a biocompatible plastic material.

The prosthesis 1 using the slotted elastic ring 4 is fitted in two stages, entirely by the endoscopic route. In a first stage, the flexible prosthesis 1 is folded up on itself to reduce its diameter and allow it to be introduced through the esophagus O with the aid of an endoscope (not shown), the fixing part 1a being positioned in the hiatal hernia H.

Once the prosthesis 1 has been positioned, a centripetal force is exerted on the slotted ring 4, for example with the aid of a forceps or a winding member of the type used by clockmakers to place a spiral spring in a spring barrel (not shown). The slotted elastic ring 4 is lowered down the esophagus O to the desired position and this ring 4 is freed, the ring tending to recover its initial cross section under the effect of its elasticity.

By virtue of the possibility of winding the slotted elastic ring 4 in a spiral to reduce its diameter, the force capable of being developed by such a slotted ring 4 is greater than that of the metal wire 2 embedded in the annular fixing part 1a of the prosthesis 1. The dimensions of the slotted ring 4 can be chosen, on the one hand, as a function of the dimensions of the hiatal hernia, and, on the other hand, as a function of the force which it is desired to obtain in the position of fixing of the prosthesis 1 in the hernia H. In a variant which is not shown, the slotted elastic ring 4 could be accommodated in an annular space formed inside the annular proximal fixing part 1a and could thus replace the elastic reinforcing element 2 embedded in this annular fixing part 1a. In this case, the annular space intended to receive the slotted elastic ring 4 must permit the winding of this ring in a spiral when a centripetal pressure is applied to the annular fixing part 1a.

For this purpose, one end of this annular space can be closed, while the other end opens onto the inner face of the annular proximal fixing part 1a. By virtue of this configuration of the annular space, when a centripetal pressure is exerted on this annular proximal fixing part 1a, one end of the slotted elastic ring 4 abuts against the closed end of the annular space, so that its other end emerges via the end of this space opening onto the inner face of the annular fixing part 1a, making it possible to reduce the diameter of the annular fixing part 1a of the prosthesis 1. By releasing the centripetal pressure, the slotted ring 4 dilates in order to recover its initial diameter. Advantageously, the end of the slotted ring adjacent to the closed end of the annular space formed in the annular proximal fixing part could be fixed to this end.

The second embodiment and its variants illustrated in FIGS. 7 through 11 relates more especially to the use of shape-memory alloy intended to stiffen the proximal end 1a of the prosthesis while the rest of this prosthesis, as far as the distal end of the tubular body 1, remains sufficiently flexible so that its walls collapse in the presence of an overpressure created by gastric reflux. In this embodiment, it is not in practice the elasticity of the material that is used, but instead its two states: soft permitting plastic deformation of the material, and relatively rigid while permitting recovery of its initial shape.

Figure 7:
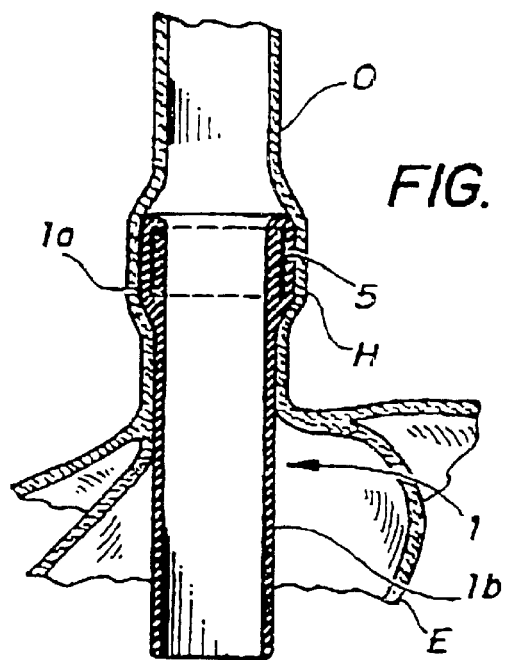
FIG. 7 is a cross section, similar to FIG. 6, of a second embodiment.
Figure 8:
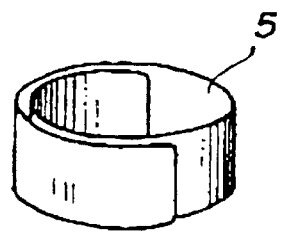
FIG. 8 is a perspective view of an element for stiffening the proximal part of the prosthesis.

The stiffening element made of shape-memory alloy 5 and illustrated in FIGS. 7 and 8 is formed by a leaf wound in a spiral. In contrast to the first embodiment, it is therefore not the elasticity of this element 5 that will be used, but its capacity to deform plastically when its temperature is lowered sufficiently, below body temperature, for it to transform to the martensitic phase in which it is relatively soft, and its capacity to recover its initial shape and to transform to the relatively rigid austenitic phase when its temperature is increased to above the temperature of the human body, in the present case above 45° C., for an alloy of 55.68% by weight Ni, and the rest Ti, in the absence of stress.

These conditions are entirely acceptable for the application envisaged. The diameter of the proximal part 1a of the prosthesis 1 must in fact be dimensioned initially to adapt to the diameter of the hiatal hernia H, and the initial diameter of the stiffening element 5 made of shape-memory alloy is dimensioned to match this diameter when it is brought to the temperature of transformation to the austenitic phase in which it is at the same time the most rigid, so that it allows the proximal end 1a of the prosthesis 1 to adapt to the hernia and prevents it from leaving said hernia.

To obtain this result, the stiffening element 5 must initially be cooled to below the temperature of the human body in order to transform to the martensitic phase so that it becomes relatively soft. In this state, it can be folded up on itself or deformed in another way in order to introduce it into the esophagus with the aid of an endoscope. Once positioned in the hiatal hernia H, it suffices to convey water at a suitable temperature or another suitable heating means in order to heat the alloy, for example to 60°, for a suitable period in order to effect the transformation of the shape-memory alloy to its austenitic phase and to cause it simultaneously to recover its initial shape in which it is applied against the wall of the hiatal hernia H. Indeed, as the stiffening element 5 of shape-memory alloy is initially dimensioned to the diameter of the hiatal hernia, no stress is exerted on it so that it can recover its initial shape.

Figure 9:
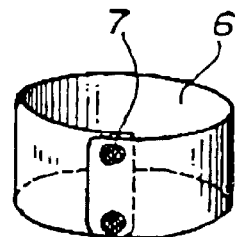
FIG. 9 is a perspective view of a variant of the stiffening element.
Figure 11:
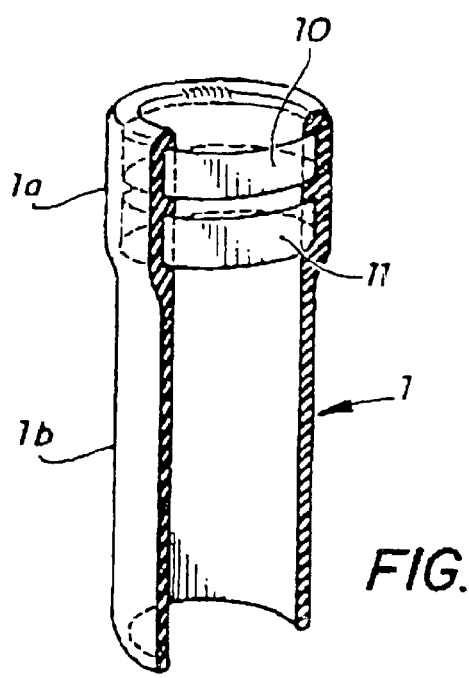
FIG. 11 is a cutaway perspective view of a prosthesis comprising a further variant of the stiffening element.
Figure 10:
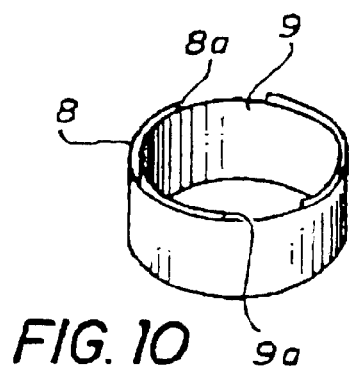
FIG. 10 is a perspective view of a second variant of the stiffening element.

To improve the stiffening conferred upon the proximal end of the prosthesis 1, it would also be possible to form a ring 6 whose two ends are fixed to one another by welding or bonding 7, as is illustrated in FIG. 9. It is also possible to use two open rings 8, 9 arranged one inside the other, the respective openings 8a, 9a of these open rings 8, 9 being offset in relation to one another by 180°. Finally, as is illustrated in FIG. 11, it is also possible to axially offset two rings of shape-memory alloy 10, 11, the annular space between these rings being able to be used to fix several suture points, for example.

What is claimed is:

1. A prosthesis comprising a generally tubular shape for controlling the direction of flow in a duct of a living organism, the prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it, and wherein said annular elastic means are formed at least partially by a slotted elastic ring, which is an independent element of said prosthesis which element is attached inside said annular proximal part.

2. The prosthesis as claimed in claim 1, wherein said prosthesis is made of elastomer, said elastic means consisting of at least one spring embedded in the elastomer of said prosthesis.

3. The prosthesis as claimed in claim 2 wherein said spring is an endless filament forming a series of regular meanders extending from one edge to the other of a ring.

4. The prosthesis as claimed in claim 2, wherein said annular proximal part encloses an annular seat, one end of which is closed, and the other end of which is open on the inner face of said annular proximal part in order to receive a slotted elastic ring.

5. The prosthesis as claimed in claim 1, wherein said annular proximal part encloses an annular seat, one end of which is closed, and the other end of which is open on the inner face of said annular proximal part in order to receive a slotted elastic ring.

6. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collaspe on itself in the presence of an overpressure exerted on its outer surface, wherein said annular proximal fixing part is associated over a certain width with stiffening means for giving it a resistance to crushing which is greater than that of the distal part of said prosthesis, the greater resistance to crushing being obtained by annular elastic means associated with this promixal part, able to retain the prosthesis by applying said annular proximal part against the wall of said section of greater diameter of said duct with a force sufficient to ensure that it is held in place as a food bolus passes through it, wherein said annular elastic means are formed at least partially by a slotted elastic ring, which is an independent element of said prosthesis which element is attached inside said annular proximal part.

7. The prosthesis as claimed in claim 6, wherein said annular proximal part encloses an annular seat, one end of which is closed, and the other end of which is open on the inner face of said annular proximal part in order to receive a slotted elastic ring.

8. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it and wherein said annular elastic means are formed at least partially by a slotted elastic ring, the prosthesis being made of elastomer, said elastic means consisting of at least one spring embedded in the elastomer of said prosthesis.

9. The prosthesis as claimed in claim 8, wherein said annular proximal part encloses an annular seat, one end of which is closed, and the other end of which is open on the inner face of said annular proximal part in order to receive a slotted elastic ring.

10. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it and wherein said annular elastic means are formed at least partially by an endless filament, the prosthesis being made of elastomer, said endless filament consisting of at least one spring embedded in the elastomer of said prosthesis.

11. A prosthesis according to claim 10 wherein said spring forms a series of regular meanders extending from one edge to the other of a ring.

12. The prosthesis as claimed in claim 11, wherein said annular proximal part encloses an annular seat, one end of which is closed, and the other end of which is open on the inner face of said annular proximal part in order to receive a slotted elastic ring.

13. The prosthesis as claimed in claim 10, wherein said annular proximal part encloses an annular seat, one end of which is closed, and the other end of which is open on the inner face of said annular proximal part in order to receive a slotted elastic ring.

14. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it, said annular proximal part enclosing an annular seat, one end of which is closed, and the other end of which is open on the inner face of said annular proximal part in order to receive a slotted elastic ring.

15. A prosthesis comprising a generally tubular shape for controlling the direction of flow in a duct of a living organism, this prostheses being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it, said greater resistance to crushing of said annular proximal part is obtained by annular elastic means associated with this proximal part, said annular proximal part enclosing an annular seat, one end of which is closed, and the other end of which is open on the inner face of said annular proximal part in order to receive a slotted elastic ring.

16. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it, and wherein said annular elastic means are formed at least partially by a slotted elastic ring; said annular proximal part enclosing an annular seat, one end of which is closed, and the other end of which is open on the inner face of said annular proximal part in order to receive a slotted elastic ring.

17. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it, and wherein said greater resistance to crushing of said annular proximal part is obtained by annular elastic means associated with this proximal part, said annular elastic means are formed at least partially by a slotted elastic ring, and said annular proximal part enclosing an annular seat, one end of which is closed, and the other end of which is open on the inner face of said annular proximal part in order to receive a slotted elastic ring.

18. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it, and wherein said prosthesis is made of elastomer, an annular elastic means consisting of at least one spring embedded in the elastomer of said prosthesis, said annular proximal part enclosing an annular seat, one end of which is closed, and the other end of which is open on the inner face of said annular proximal part in order to receive a slotted elastic ring.

19. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it, and wherein said greater resistance to crushing of said annular proximal part is obtained by annular elastic means associated with this proximal part, wherein said prosthesis is made of elastomer, said elastic means consisting of at least one spring embedded in the elastomer of said prosthesis, said annular proximal part enclosing an annular seat, one end of which is closed, and the other end of which is open on the inner face of said annular proximal part in order to receive a slotted elastic ring.

20. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it, wherein said greater resistance to crushing of said annular proximal part is obtained by annular elastic means associated with this proximal part, and wherein said annular elastic means are formed at least partially by a slotted elastic ring, said prosthesis being made of elastomer, said elastic means consisting of at least one spring embedded in the elastomer of said prosthesis, said annular proximal part enclosing an annular seat, one end of which is closed, and the other end of which is open on the inner face of said annular proximal part in order to receive a slotted elastic ring.

21. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it, wherein said greater resistance to crushing of said annular proximal part is obtained by annular elastic means associated with this proximal part and wherein said annular elastic means are formed at least partially by a slotted elastic ring, and wherein said slotted ring is an independent element of said prosthesis which element is attached inside said annular proximal part, and wherein said prosthesis is made of elastomer, said elastic means consisting of at least one spring embedded in the elastomer of said prosthesis, said annular proximal part enclosing an annular seat, one end of which is closed, and the other end of which is open on the inner face of said annular proximal part in order to receive a slotted elastic ring.

22. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it, wherein said prosthesis is made of elastomer, an elastic means consisting of at least one spring embedded in the elastomer of said prosthesis, and wherein said spring is an endless filament forming a series of regular meanders extending from one edge to the other of a ring, said annular proximal part enclosing an annular seat, one end of which is closed, and the other end of which is open on the inner face of said annular proximal part in order to receive a slotted elastic ring.

23. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it wherein said greater resistance to crushing of said annular proximal part is obtained by annular elastic means associated with this proximal part and wherein said prosthesis is made of elastomer, said elastic means consisting of at least one spring embedded in the elastomer of said prosthesis, wherein said spring is an endless filament forming a series of regular meanders extending from one edge to the other of a ring, said annular proximal part enclosing an annular seat, one end of which is closed, and the other end of which is open on the inner face of said annular proximal part in order to receive a slotted elastic ring.

24. A prosthesis comprising a generally tubular shape for controlling the direction of flow in a duct of a living organism, this prosthesis being made of a biocompatible, elastically deformable material and comprising an annular proximal fixing part in a section of greater diameter of said duct, and a distal part whose wall is dimensioned to allow it to collapse on itself in the presence of an overpressure exerted on its outer surface, wherein said annular proximal fixing part is associated over a certain width with stiffening means for giving it a resistance to crushing which is greater than that of the distal part of said prosthesis, able to retain the prosthesis by applying said annular proximal part against the wall of said section of greater diameter of said duct with a force sufficient to ensure that it is held in place as a food bolus passes through it wherein said greater resistance to crushing of said annular proximal part is obtained by annular elastic means associated with this proximal part, said annular elastic means being formed at least partially by a slotted elastic ring, said prosthesis being made of elastomer, said elastic means consisting of at least one spring embedded in the elastomer of said prosthesis, said spring is an endless filament forming a series of regular meanders extending from one edge to the other of a ring, wherein said annular proximal part encloses an annular seat, one end of which is closed, and the other end of which is open on the inner face of said annular proximal part in order to receive a slotted elastic ring.

* * * * *